United States Patent [19]

Miller

[11] Patent Number: 5,509,888
[45] Date of Patent: Apr. 23, 1996

[54] CONTROLLER VALVE DEVICE AND METHOD

[75] Inventor: Paul L. Miller, Minnetonka, Minn.

[73] Assignee: Conceptek Corporation, Wilmington, D.C.

[21] Appl. No.: 281,226

[22] Filed: Jul. 26, 1994

[51] Int. Cl.⁶ .................................................. A61F 2/00
[52] U.S. Cl. ............................... 600/29; 128/DIG. 25
[58] Field of Search ..................... 600/29–32, 38–41; 128/DIG. 25

[56] References Cited

U.S. PATENT DOCUMENTS

| | | | |
|---|---|---|---|
| 3,642,004 | 2/1972 | Osthagen et al. | 128/DIG. 25 |
| 3,812,841 | 5/1974 | Isaacson | 128/1 R |
| 3,939,821 | 2/1976 | Roth | 600/30 |
| 5,004,454 | 4/1991 | Beyar et al. | 600/30 |
| 5,041,092 | 8/1991 | Barwick | 600/29 |
| 5,140,999 | 8/1992 | Ardito | 128/885 |

Primary Examiner—Angela D. Sykes
Assistant Examiner—John P. Lacyk
Attorney, Agent, or Firm—Albert C. Smith

[57] ABSTRACT

Device and method for regulating fluid flow within the human body includes small electromagnetic devices embedded in an inner housing of the present device that function under the control of a programmable control unit to create small magnetic fields which cause an artificial increase in the viscosity and apparent density of a magnetorheological fluid located in a compartment surrounding the structure through which fluid flow is to be controlled.

30 Claims, 6 Drawing Sheets

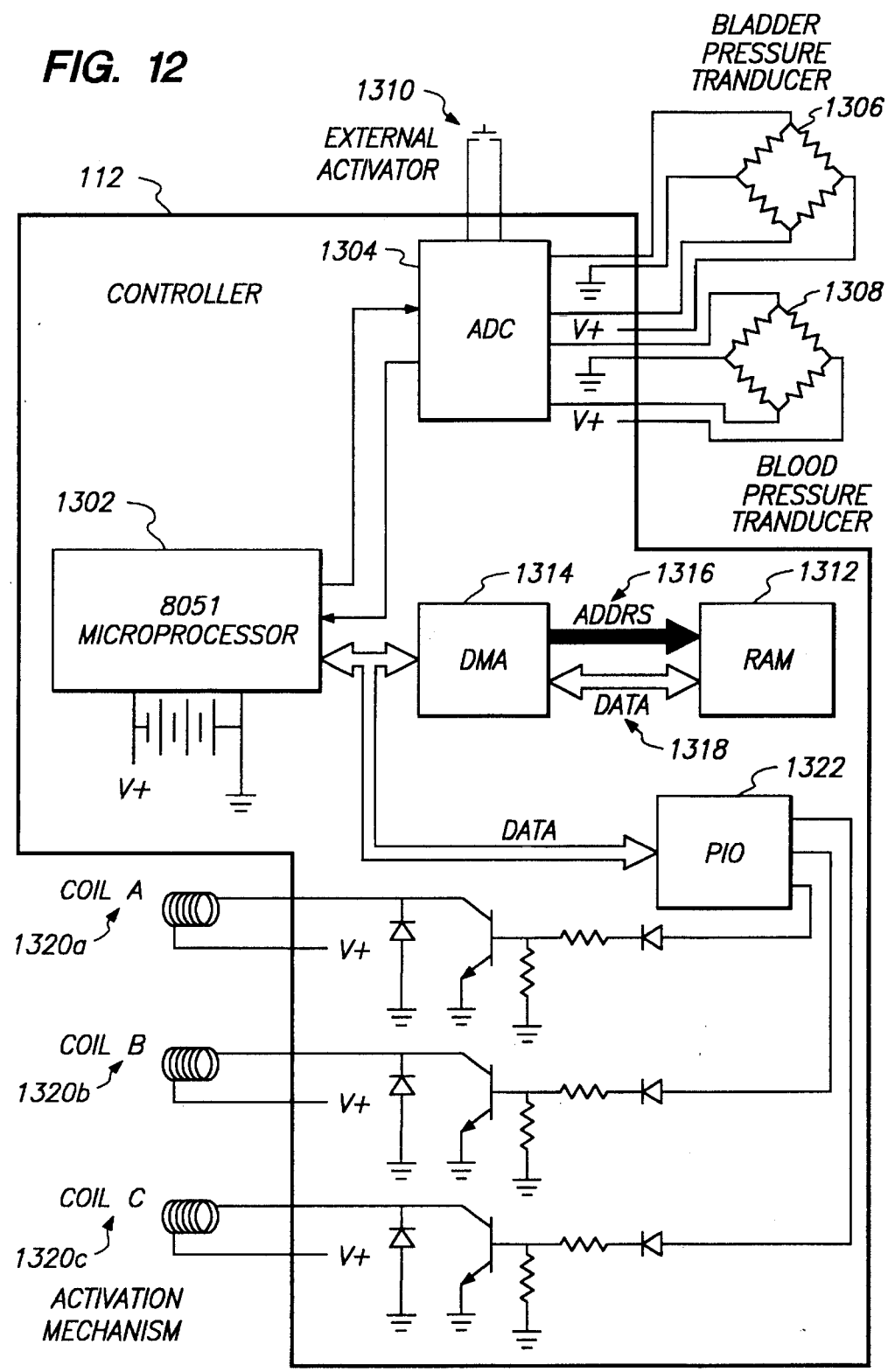

CONTROLLER VALVE DEVICE AND METHOD

BACKGROUND OF THE INVENTION

1. Field of the Invention

The invention relates generally to valve devices for controlling the flow of fluids and substances within the human body, and relates more specifically to such valve devices and methods for use in controlling urinary and bowel incontinence.

2. Description of Background Art

Urinary incontinence is a dysfunction of the bladder to securely retain urine until the individual intends to void. Causes for urinary incontinence are many and affect all age groups, but tends to be more prevalent among females and the elderly. The major forms of incontinence are stress incontinence, psychogenic incontinence, and trauma, typically surgical, to the vesicle neck. Urinary incontinence is currently estimated to affect about 4% of the population, a figure that is growing due to population shifts toward longer life spans. At the present time, the direct and indirect costs related to urinary incontinence are estimated at between $1.8 and $10 billion per annum in the U.S.

Present methods for treating urinary incontinence are pharmacological, surgical, behavioral, and prosthetic implant devices. The least intrusive treatment that can achieve desired results always is recommended. However, each of the existing treatments have limitations and drawbacks. The behavioral treatment is useful in cases of minor dysfunction, while exercises can help minimize the effects in stress incontinence. The use of a prosthetic device has, historically, been less desirable as these devices can cause irritation to the sensitive sections of the urethra and ultimately necrosis should the prosthetic device result in circulatory insufficiency. In addition, application of the obturating collars of the older devices required that the urethra be severed and reattached, further complicating the surgical procedure and causing additional trauma to the tissue. Other forms of incontinence, such as bowel incontinence, require similar treatments.

There are several other environments in which fluid control within the human body is desirable. For example, impotence often is the failure of blood flow to the superficial and/or deep dorsal veins of the penis. Several penile implants are commercially available, all of which include some type of local trauma to the region. It would be a benefit to control fluid flow remotely and permanently with a reduced trauma to a localized region.

The leading penile implant on the market is available from AMS (Minnetonka, Minn.). That implant includes a pair of silicone cylinders that are surgically implanted in the penile corpus and attached to a pump placed in the scrotum. Erection is achieved by digitally locating the pump and manually pumping silicone fluid into a set of inflators. An internal "bleed-down" orifice allows the fluid to return to the reservoir at a controlled rate. This device is awkward to operate, places substantial amounts of hardware in physiologically and psychologically sensitive areas, and places unnecessary pressure on the tissues surrounding the inflators.

An alternative penile implant device includes a penile rod that simply is a plastic rod that is forcibly inserted by the individual into a surgically fabricated fold of skin along the side of the penis. Although functional, the device is capable of injuring delicate tissues if inserted incorrectly and has additional problems associated with maintaining the skin fold in a state of cleanliness.

At present, existing control mechanisms for human body fluids, such as blood, urine, and the like, are large and cumbersome, and cause significant trauma at the functional location. Such artificial control valves for bodily functions are a continuing source of problems for the medical industry. The tissue around the sphincters, or naturally occurring valves, are not designed to be deprived of blood flow or perfusion for long periods of time. This sensitivity to external constriction has caused most of the artificial devices to at least callous the area or render the tissue to a necrotic state.

One conventional inflatable cuff, also available from AMS, is designed for positioning about the urethra and has a binary control which allows the cuff to be fully inflated, then fully deflated at selected intervals. This artificial urethral sphincter is a silicone toroid that is positioned around the urethra. Applying the device involves severing the delicate urethra and threading the urethra through the hole in the device. The procedure is complicated by a restricted workspace and, in the case of females, the short length of the urethra. Upon inflation of the positioned device by an attached pressurizing device, the artificial cuff inflates and the interior surface of the toroid constricts the external surface of the urethra, collapsing the interior duct. Given that the average adult urinates only four times daily, the urethra is in a constricted state without blood flow for approximately six hours at a time. The combined effects of depriving the tissue of adequate perfusion for extended periods of time and being positioned in a sensitive area with an exposure to bacterial agents, results in poor long term viability for the urethra. The remedial action is to have the urologist surgically remove the necrotic area and reattach the urethra. Since there is a finite amount of urethra, the number of reattachments is limited.

Thus, there remains a need for an implantable control valve for selectively controlling fluid flow within the human body.

SUMMARY OF THE INVENTION

In accordance with the present invention, an active device that regulates fluid flow within the human body is described. Small electromagnetic devices are embedded in one embodiment of the present invention and function under the control of a programmable control unit. Small magnetic fields are created by the electromagnetic devices to cause an artificial increase in the viscosity and apparent density of a magnetorheological liquid located in a compartment surrounding the structure through which fluid flow is to be controlled.

Preferably, the magnetorheological liquid includes small ferrous spheroids approximately 5 microns in diameter. Such biologically inert colloidal spheroids are suspended in an inert paraffinic fluid vehicle to form a magnetorheological fluid. An increase in the viscosity and density of the fluid causes a temporary restriction in the free space separating the structure to be controlled from the device and constrictively occlude the flow of fluid through the structure.

More specifically, the present invention includes a controllable valve device for operation about a constrictable passageway. The device includes a flexible, formable, tubular housing of predetermined length. The housing contains an extensible inner chamber extending at least partially along the length of the housing and at least one magnetic flux inductor proximal to the inner chamber. The device further includes a control device, in communication with the magnetic flux inductor device for selectively activating the magnetic flux inductor device. A quantity of magnetorheological material responsive to the activation of the magnetic flux inductor is contained within the inner chamber such that activation of the magnetic flux inductor causes the magnetorheological material to outwardly extend the inner chamber and constrict the passageway.

BRIEF DESCRIPTION OF THE DRAWINGS

FIG. 12 is a schematic diagram of a microprocess controller that may be included in the present invention.

DETAILED DESCRIPTION OF THE PREFERRED EMBODIMENTS

Figure 1A:
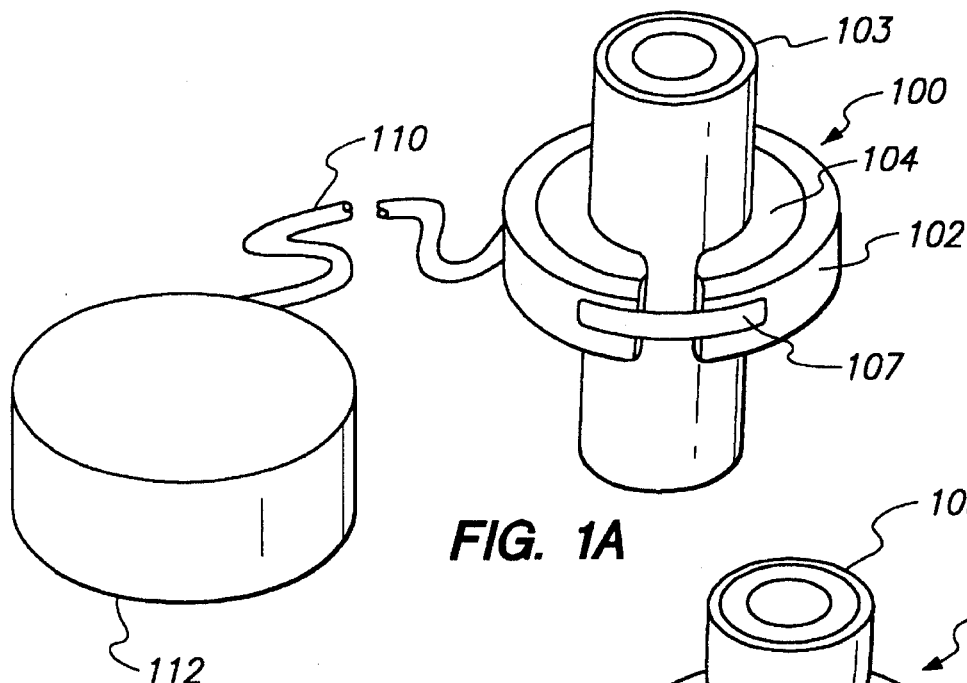
FIG. 1A shows a perspective view of an embodiment of the control valve of the present invention in a relaxed state.
Figure 1B:
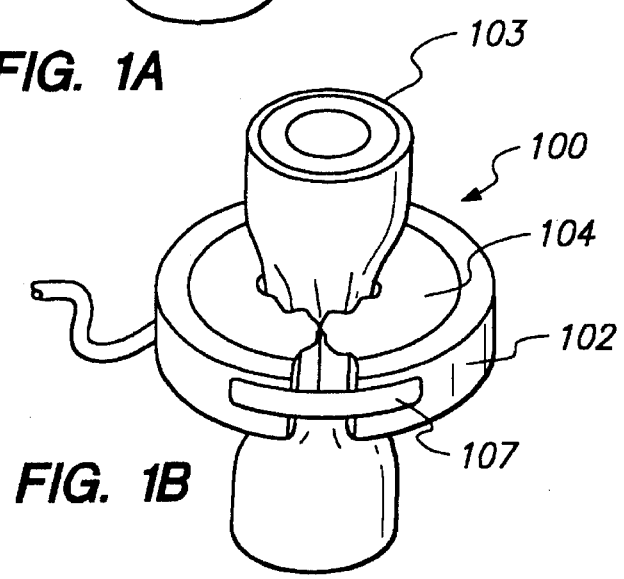
FIG. 1B shows the embodiment of FIG. 1A in an expanded, activated state.

The present invention is a controllable valve device 100 for operation about or within a constrictable passageway. The device 100 includes a flexible, formable, tubular housing 102 of predetermined length. As shown in FIGS. 1A and 1B, the housing 102 may be formed in the shape of an open circle to enable positioning about a passageway. In alternate embodiments, the housing may be in the shape of a closed circle, for insertion within a passageway, or may be in other shapes best suited for the particular passageway 103 which the device 100 constricts.

FIG. 1A shows the device 100 in its uninflated, non-constricting form, whereas FIG. 1B shows the same device 100 in its inflated form constricting the passageway 103. In the illustrated embodiment, the device 100 includes a gate closure 107 device that secures the housing 102 around the passageway.

The device housing 102 may be manufactured from any material that is substantially rigid, yet formable. Exemplary materials include: titanium or titanium alloys, such as Ti-6Al 4V; cobalt-based ferrous alloys; nickel alloys, such as nickel-titanium alloys, including NITINOL (which is an alloy of nickel (Ni) and titanium (Ti) developed by the Naval Ordinance Laboratories (NOL) at Silver Spring, Maryland, commercially available from Raytheon, Menlo Park, Calif.); ceramic materials, such as high-density aluminum oxide; carbon compounds such as pyrolytic carbon, vitreous carbon, or vapor deposited carbon on substrates; and plastic materials, such as medical grades of polyethylene, polypropylene, perfluorinated polymers, acrylic polymers, polyurethanes, or silicone rubbers.

The housing 102 prevents the ingress of bodily fluids into the electrical or mechanical mechanisms of the control portion of the device. Human body fluids are extremely corrosive to materials and few materials are able to withstand both the chemical and biological attack. In a preferred embodiment, the housing 102 is impervious to all biological and chemical attack. A preferred material is titanium ahoy Ti-6Al-4V based on its strength, formability, and long-term acceptance by the body fluids. For embodiments which will be implanted in a human body, the housing material must be biocompatible.

Figure 2:
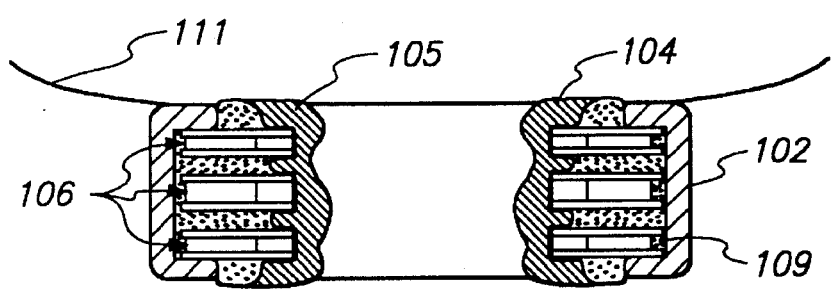
FIG. 2 shows a cross-section view of the embodiment of FIG. 1A and 1B.

The housing 102 holds an extensible inner chamber 104, as shown for example in FIG. 2. The inner chamber 104 includes a pliable membrane, preferably manufactured from a biologically inert material capable of withstanding the pressures related to actuation of the device, as described in further detail below. Exemplary materials for the inner chamber 104 include perfluorinated polymers, polyurethanes, and silicone rubbers.

The chamber 104 contains an amount of a magnetorheological fluid 105. Preferably, such liquid contains ferrous microspheroids suspended in a biologically inert paraffinic fluid vehicle, such as a paraffin-based solution. The magnetorheological liquid 105 is based on the magnetic properties of a colloidal suspension of magnetically responsive materials in a carrier liquid. This liquid may have a base of water, hydrocarbons, esters, diesters, polyphenylethers, fluorocarbons, and the like. For medical applications, an inert carrier liquid such as aqueous, hydrocarbons or fluorocarbons are preferred. It also is desirable that the liquid be inert with the containment materials and preferably is immiscible with the human body fluids.

The magnetic colloid may either be a metallic based particle, such as ferrites or magnetite, or based on ceramic particles such as ceramic magnetic powders. The diameters of such ultrafine particles typically are measured in nanometers, with a wide range of useful sizes, depending on the particular application. The particles may be coated with a surfactant to stabilize the colloidal suspension. Magnetorheological fluids 105 of the type that may be used in conjunction with the present device 100 are manufactured by, and commercially available from several sources, including the Ferrofluidics Corporation (Nashua, N.H.). The surfactant component may depend on the particular application. In a preferred form of the magnetorheological suspension, ferrous particles in a range of about 4 to about 40 nanometers in diameter are suspended in a steric acid surfactant with an aqueous carrier.

Proximal to the chamber 104 is one or more electromagnetic induction devices 106, separated by potting material 109, which exert a magnetic force on the metallic particles contained in the chamber 104 when suitably activated. Electromagnetic induction devices 106 are fine, insulated wire coils embedded in an inert potting agent 109, such as acrylic polymers, polyurethanes, or silicone rubbers. The wires typically are between about 30 to about 100 AWG (American Wire Gauge), with the number of rams determined by the mathematical relationship of magnetic force being measured as ampere turns per meter. Fixing the electrical current (amperes) and fixed magnetic flux gap (distance the magnetism must couple between the coil and the magnetorheological fluid) allows the designer to adjust the number of rams to proportionally increase or decrease the intensity of the magnetic field.

Figure 3:
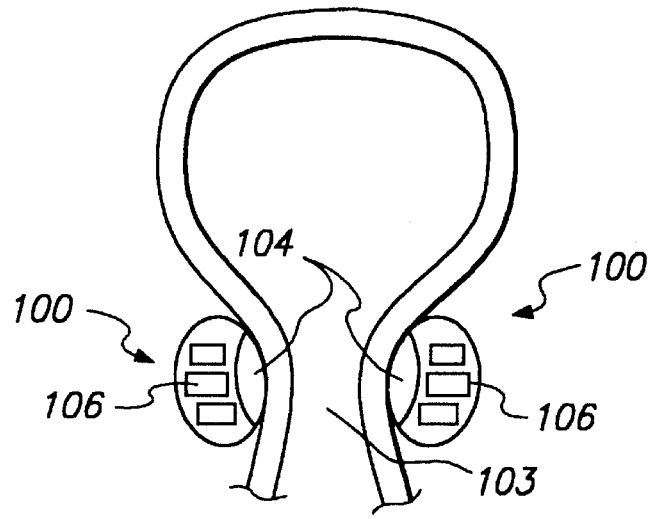
FIG. 3 shows a cross-section view of the embodiment of FIG. 1 in position about the urethra and below the bladder, for operation of the control valve device to control urinary incontinence.

In one embodiment, the inductors 106 use 1000 turns of 50 AWG wire potted in acrylic polymer and a 0.0001 meter flux gap. This allows the control unit 112 to vary the electrical current (amperes) to control the intensity of the magnetic field. The coils are wound around a silicon steel armature. The armature concentrates the magnetic flux and allows greater precision in placing the activating magnetic fluid in a desired location. The number of these coils are determined by a function of force required, size of coils, size of operational area, and number of stages that need to be activated. In one embodiment of a urinary incontinence control device (for example, as shown in FIG. 3), three layers of coils may be used, one for each stage, for a total of eighteen coils. These coils are attached to the interconnecting wiring 110, or control lines, by either microscopically soldering, welding, or crimping the coil wires to the control fines 110.

Preferably, a series of such electromagnetic devices 106 are positioned along one side of the chamber 104, to create small magnetic fields along the edge of the chamber 104 when activated. Activating the devices 106 causes an artificial increase in the viscosity and apparent density of the magnetorheological fluid 105. The increase in viscosity and density of the fluid 105 causes a temporary restriction in the free space separating the passageway 103 from the device 100, as illustrated in FIG. 1B. By positioning a series of such devices 106 along one side of the chamber 104, activation of selected ones of the devices 106 in a cyclic sequence may emulate peristaltic movement that is transferred to the passageway 103.

In a preferred embodiment, a microcontroller, such as an Intel 8031/8051 or a Motorola 6000 series, may be used in the control unit 112 to control the electromagnetic induction devices 106. However, other microcontrollers such as programmable logic devices (PLD) and gate array logic (GAL) devices may be used. In alterative embodiments, it may be possible to have a combination of controllers 112 both internal and external to the electromagnetic induction devices 106. The controller unit 112 may be programmed to activate the induction devices 106 at predetermined times and in selected sequences, at predetermined intensities, or at alternating times and intensities for selected ones of a series of devices 106.

**An exemplary microprocessor controller unit 112 that may be used in conjunction with the present device 100 is shown in FIG. 12. That illustrated unit 112 includes a microprocessor (1302), such as an Intel 8051, that uses a computer control program stored in a built-in read-only memory, or ROM microcircuit. The microcontroller 112 interfaces with other components through a serial data communication port to an analog-to-digital converter (1304) that converts analog electrical signals to digital information in order for the microcontroller to properly interpret bladder and blood pressure via microcircuit-based pressure transducers (1306 and 1308, respectively), such as those manufactured by SenSym (Sunnyvale, Calif.).

Additional data is fed from an external activator (1310) into the microcontroller 112 via the ADC (1304) identifying to the microprocessor (1302) the need to perform an alternative software program, such as bladder voiding. As part of the software program, certain calculations may be performed that are temporarily stored in a random-access memory (RAM) device (1312) that is accessed by the microprocessor (1302) via a data-management accessory (DMA) (1314) that monitors the address bus (1316) and data bus (1318). The function of the RAM (1312) is to store information that the microprocessor (1302) will utilize at some future time. The microprocessor (1302) interfaces its control of the activation mechanisms (1320a, 1320b, 1320c) by means of a parallel input-output (PIO) (1322) device. The control operations, driven by digital commands from the microprocessor (1302), cause the individual activation mechanisms (1320a, 1320b, 1320c), such as activation coils, to function by means of the PIO (1322) activating transistors connected to the activation mechanisms (1320a, 1320b, 1320c).

Figure 4:
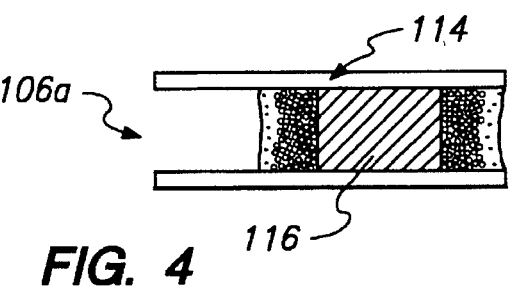
FIG. 4 shows a cross-section view of an electromagnetic device that may be used in an embodiment of the present invention.

FIG. 4 shows a detailed drawing of an exemplary induction device 106' that may be used in the present device 100, as shown in FIG. 2. The illustrated inductor 106' includes a pole section 114 that may be used to secure the device 106' into position within the housing 104. That device 106' includes an inductor core 116, surrounded by magnetic coils 118. Potting material 109 surrounds the coils 118 to insulate and secure the wire coils 118 in place.

A microprocessor controlled device may also be used for monitoring blood pressure and adjusting the applied pressure in proportion to the blood pressure. Alternatively, such devices may be used for monitoring internal fluid pressure on the internal aspect of the flow control device and adjusting the applied pressure accordingly. Another use for such devices includes monitoring internal body conditions, through various sensors, and/or external commands, transmitted transcutaneously, and processing the correct functional response based on either preprogrammed algorithms or by learned synthetic intelligence, or artificial intelligence, within its microprocessor. The device may monitor its own performance, perform its own diagnostic, and communicate with external diagnostic equipment to report on its "health". The device also may monitor its own performance and initiate a controlled shut-down of functions if the state of degradation is non-serious, or to safely inactivate itself to prevent serious failure situations.

In another embodiment, the user may have control of the electromagnetic induction devices 106 by use of a switch, such as a simple push button, that either activates or deactivates the devices 106. All three types of controllers 112 may work together with certain controls having ultimate command, depending upon safety-critical functional considerations. Electrical energy for driving the electromagnetic induction devices 106 may be derived from one of three sources: stored energy sources, such as batteries that are positioned or implanted with the device 100; external sources of power transmitted via trans cutaneous coupling, such as via radiofrequency, magnetic flux, photoconduction, or electrical feed-throughs; or internally generated power by electrochemical action, such as fuel cell operation, or by electromechanical actions, such as piezoelectric film disposed in a highly mobile area. Other power sources may also be used, depending on the specific application.

Figure 5:
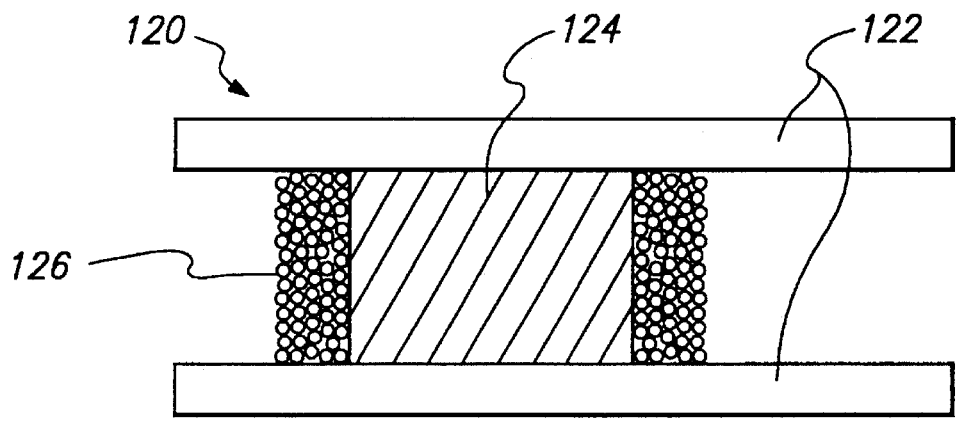
FIG. 5 shows a cross-section view of a counter-electromagnetic force system using electricity that may be used in an embodiment of the present invention.

FIG. 5 shows an exemplary counter-electromagnetic force system 120 that may be used as an inductor in the present device 100 using electricity as the energy source. In that illustrated system 120, two pole pieces 122 are included to secure the system 120 within the inner housing 104 of the device 100. A permanent magnet 124 is surrounded by copper wiring 126 which may then be electrically charged using an energy source (not shown) attached to the poles 122. The permanent magnet 124 is "demagnetized" by the application of electricity flowing through the wire coil 126. The effect of the demagnetizing force is to release the effect of magnetism on the magnetorheological fluid, thus defining a "counter-electromagnetic" force system 120.

Figure 6:
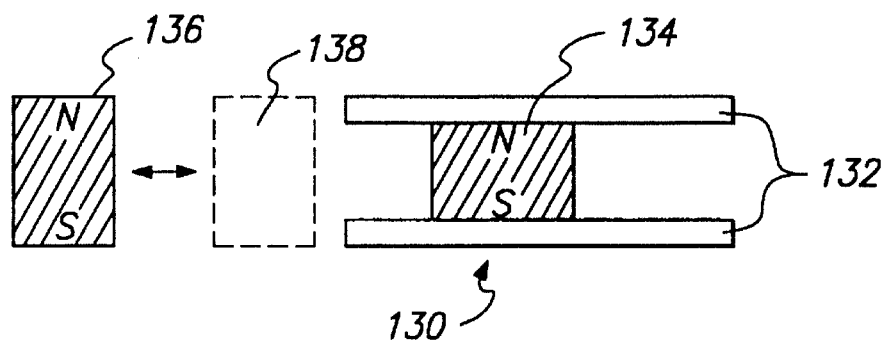
FIG. 6 shows a cross-section view of a counter-electromagnetic force system using magnetism that may be used in an embodiment of the present invention.

In an embodiment having mechanical action actuated by the device 100, motive power may come from pneumatic, hydraulic, linear, or rotary actuators in lieu of electromagnetically controlling the magnetorheological fluids 105. The fluids 105 may be activated mechanically by introducing the magnetic field of a permanent magnet 134, in lieu of electrically energizing the electromagnetic field of an electromagnet, or induction coil. FIG. 6 shows an exemplary counter-magnetic force system 130 that uses magnetism as the activating energy. In that system 130, the poles 132 are channels for the magnetic flux to preferentially flow therethrough. Ferrous materials are approximately 900 times as magnetically permeable as biological tissue. The magnetic flux can effectively be nullified by the application of a second magnet 136 of equal strength but of opposite polarity brought into contact with the pole pieces 132.

In one mode of operation, a counter-electromagnetic force generated by an electrical field is applied to an electromagnet to counterbalance the magnetic field of a permanent magnet 134. This counter-electromagnetic embodiment is based on using an opposing magnetic force to nullify an existing magnetic field developed by a permanent magnet 134. The opposing magnetic field would be generated by electric current energizing an electromagnet and would cancel the existing magnetic field when the flux levels were exactly matched, but in opposite polarity. In this manner, the magnetic force normally would be applied to the magnetorheological fluid 105 by permanent magnets 134 and would be deactivated by an electric current. An analogy is a normally closed (NC) electric switch or valve that will only shut off or open by applying power to deactivate the switch or valve. In such a manner, the device 100 may be characterized as a normally closed device which becomes deactivated only on user command.

This illustrated system 130 may be controlled by the individual user or by some mechanical or logical devices. Connection for these system 130 may be through linear actuators, such as tubing carrying pneumatic or hydraulic force, or through push-rod connections for the transmission of mechanical energy, such as either solid links or cables. In addition, rotary devices may utilize rotating shafts to rotate the permanent magnets into and away from proximity to the magnetotheological fluids, in contrast to a linear motion device for moving the permanent magnet toward and away from the fluid.

In embodiments requiring interconnecting wiring 110, such wiring 110 may include a noble metal that is biologically inert. Such materials include gold or one of the platinum-group metals. As an alternative, silver or copper conductors may be protectively clad with a biologically inert metal or polymer material to afford protection against human toxicity. Insulation for such wiring may be manufactured from a medical grade plastic, such as polyethylene, polypropylene, perfluorinated polymers, acrylic polymers, polyurethanes, and silicone rubbers.

The present device 100 may be used in a wide variety of applications and modes of operation. A preferred application of the present device 100 is to control urinary incontinence. In that embodiment, the device 100 enables the pulsation of a magnetorheological clamping force on the passageway 103, provided by the selective activation of the electromagnetic induction device 106, to allow perfusion of blood into affected areas. In another mode, the device 100 accurately varies the compressive force of the constriction on the passageway 103 to minimize unnecessary force. The device 100 may dynamically vary the compressive force in response to either changes in intra-bladder pressure or changes in systemic blood pressure. This dynamic adjustability allows for control of urine or other fluid through the passageway 103 without the prevention of blood perfusion in the area surrounding the passageway 103. Finally, several devices 100 may be arranged to actively "pump" urine against normal bladder pressure back into the bladder in peristaltic manner to minimize leakage. A beneficial side effect may be that the dynamic movement of the peristaltic pumping action encourages distal perfusion of the urethral tissue in the area of constriction.

The device 100 may be used in several modes of operation. In a fast mode, electrical energy is applied to the magnetorheological fluid 105 in a controlled manner. This is achieved by placing an electrical conductor proximal to a highly permeable material such that the conductor concentrates in the magnetorheological fluid 105 the magnetic flux generated by electrical current flowing in the conductor. A typical conduction method would allow the flow of electricity through a copper conductor wrapped around an armature of high permeability.

In one embodiment, the device 100 is normally open, to assure that the default setting of the device permits fluid flow through the passageway 103 until the magnetic induction devices 106 are activated. In an alternative embodiment, the device 100 is normally closed, to prevent fluid from flowing through the passageway 103 until the magnetic induction devices 106 are activated. In yet another embodiment, the device 100 includes a combination of these two settings, such that it is normally closed, but if the energy source becomes depleted, the device 100 becomes a normally open device. Such an embodiment may be preferred for use as a urinary or bowel incontinence device. The specific configuration will depend on the particular application.

In another mode of operation, a permanent magnetic device is physically moved into proximity of the magnetorheological liquid to activate the liquid. This mode does not require the use of electricity, but is dependent on the appropriate positioning of a constant magnet energy source. The physical movement of a permanent magnet in proximity to the magnetorheological fluid 105 would be sufficient to activate the fluid 105. The distance necessary between activation and deactivation is dependent on the strength of the permanent magnet and the sensitivity of the magnetorheological fluid. This type of device 100 may be classified as a normally open device.

Alternatively, the permanent magnet device may be moved away from the fluid 105 to release the fluid 105 from operation. This type of device 100 may be classified as a normally closed device. Alternatively, a permanent magnet 134' may physically be moved proximal an existing permanent magnet 134 of opposite magnetic polarity to nullify the effect of the magnetic flux on the fluid 105 to deactivate the fluid 105. Just as electromagnets may be used to nullify the magnetic flux of the first permanent magnet 134, another permanent magnet 134' may be used to cancel out the magnetic field of the furst magnet. Achieving cancellation of the magnetic flux requires that the second magnet 134' have sufficient B-field energy over the coupling distance to the furst magnet 134, and opposite polarity in order to neutralize the B-field of the first magnet 134. This application of counter-magnetic force using permanent magnets 134,134' would best be applied by mechanically moving the disrupting magnet into the magnetic field to disrupt the function of the magnetorheological fluid. This type of device 100 may be classified as a normally closed device.

The following are exemplary applications of the inventive device 100.

EXEMPLIFICATION

EXAMPLE 1:

Urinary incontinence device

As a prosthetic urinary incontinence device, and referring now to FIG. 2, the present inventive device 100 includes a nearly circular occlusive collar housing 102 containing a plurality of magnetic induction devices 106. The magnetic induction devices 106 may be secured in an inner housing 104 by potting the devices with a suitable material 109 to render them both inert and immobile. Such materials suitable for this task include generally commercially available acrylic polymers, polyurethanes, and silicone rubbers. The induction devices 106 are positioned proximal an amount of magnetorheological material colloidally suspended within an inert fluid vehicle.

The magnetorheological fluid 105 includes small ferrous spheroids approximately 5 microns in diameter. These biologically inert colloidal spheroids are suspended in an inert paraffinic fluid vehicle to form the magnetorheological fluid confined within the housing 102.

A control unit 112 for the activation and deactivation of a series of magnetic induction devices 106 operating within the occlusive housing 102 may be positioned in several places. For example, the control unit 112 may be positioned inside the collar housing 102 or outside the collar housing, but still within the body cavity, or external to the body entirely. In a preferred embodiment, the control unit 112 is positioned outside the collar housing 102, but still within the body cavity. Three induction devices 106 are positioned about the inner chamber 104 containing an amount of magnetorheological fluid 105. An energy source is used to supply electrical power to the control unit 112. An exemplary source may be a medically approved lithium battery pack having lithium batteries sealed within a biologically inert container, as manufactured by Honeywell Power Sources Center (Horsham, Penn.).

The device 100 is positioned around the urethra, and functions to occlude the urethra upon selective activation of the magnetic induction devices 106. The circular design of the housing 102 permits positioning of the device 100 around the urethra without separating the urethra, thus minimizing trauma to the patient during introduction and implantation of the device 100. The shape of the collar housing 101 allows the unsevered urethra to pass safely through the gap in the distal portion before the gap is closed and latched. The compact size of: the device 100 and the distal gap allows the insertion of the device 100 without major surgery or dislocation of the urogenital structures. The superior surface of the collar housing 102 is supplied with an attached skirt 111 of surgical Dacron to allow the surgeon to attach the collar firmly to the external fundus of the bladder and to allow the natural healing process to attach the inert skirting to the bladder. This attachment process prevents the device 100 from rubbing against the bladder and minimizes subsequent localized irritation or trauma.

Upon activation of the magnetic induction devices 106, the viscosity and density of the magnetorheological fluid 105 increases, causing the housing 102 to expand inwardly and to apply pressure against the outer walls of the urethra. This causes a temporary restriction in the free space separating the urethra from the device 100 to constrictively occlude the flow of urine while maintaining the clamping force below that of the patient's systolic blood pressure. The temporary restriction below systolic blood pressure does not inhibit blood perfusion to the surrounding tissue, thus reducing the incidence of necrosis in that area.

Movement of the magnetorheological fluid 105 in a direction toward the bladder may be achieved by selectively activating ones of the magnetic induction devices 106 in a peristaltic-like manner. This action allows distal re-perfusion of the previously occluded area of the urethra, preventing necrosis of the urethral lining and musculature. Cycling time for this movement of the magnetorheological liquid may be adjusted by the physician for optimal urine retention and minimal damage to the urethral tissue.

EXAMPLE 2

Penile implant

Figure 7:
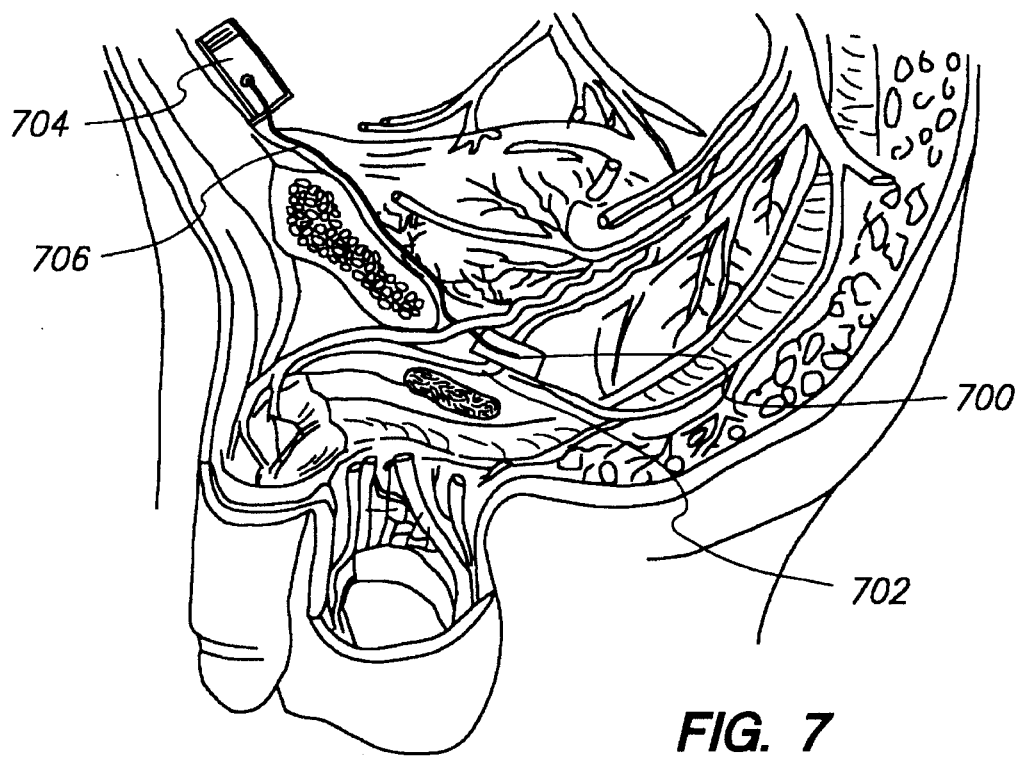
FIG. 7 shows a partial cut-away view of a human cervical region showing a penile implant embodying the present invention positioned therewithin.

This exemplary device 700, as illustrated in FIG. 7, controls the flow of blood from the superficial and/or deep dorsal veins 702 of the penis, allowing erection due to the arterial engorgement of the corpus cavernosum penis. The actuation mechanism, under the control of a control unit 704 similar to that described above in detail, can be remotely located from the device 700 either within or outside of the body. The control unit 704 may contain the microcontroller, microelectronic interface circuitry, and an energy source such as a lithium battery pack. This unit 704 may be connected by control wires 706 to the obturating device 700 on the veins.

Upon external activation by the user, the command unit 704 begins the sequence of events that allow normal erection to occur. This external activation signal may be in the form of digitally depressing a momentary contact switch located subcutaneously, a transcutaneous radio-frequency transmission from a manually activated transmitter, or a transcutaneous induced capacitance sensor that detects the presence of another person. The microcontroller activates the magnetorheological fluid 105 located in the obturating inner housing 104 located around the superficial and deep dorsal veins 702. The closure of most of the venous return from the penis allows full erection to occur as it does naturally. The control unit 704 monitors for some secondary preprogrammed event to occur prior to releasing the obturating inner housing 104 to their quiescent position. This secondary event may be ejaculation, with an appropriate time delay, loss of proximity contact for greater than some preset time, secondary activation of the activation switch to cancel erection, or simply erection time exceeding a preset limit.

The device 700 used in this illustrated embodiment may be constructed substantially similar to that described above. This exemplary device 700 allows the restoration of normal penile function and acts as a permanent prosthetic device.

EXAMPLE 3

Bowel incontinence valve

Figure 8:
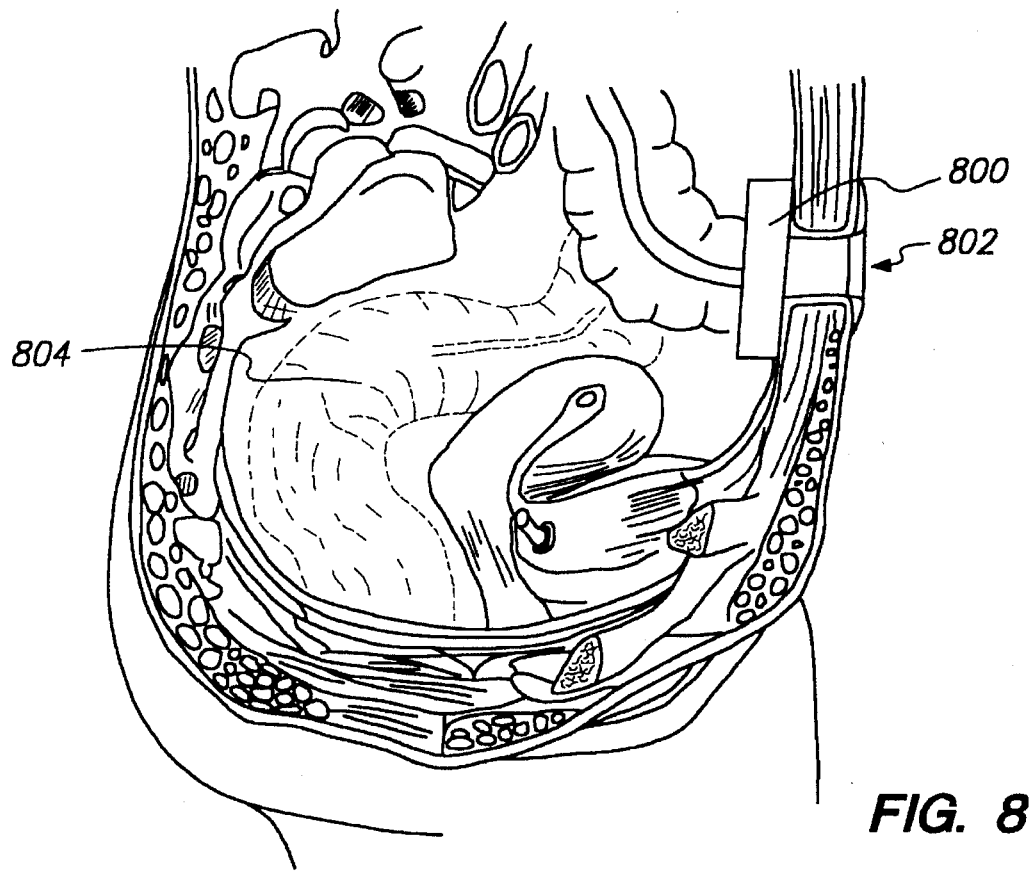
FIG. 8 Shows a partial cut-away view of a human cervical region showing a bowel incontinence control device embodying the present invention positioned therewithin.

In this exemplary embodiment, as illustrated in FIG. 8, the device 800 includes a pliable inner chamber 104 filled with magnetorheological fluid 105 and a surrounding actuation mechanism in a manner similar to that described above with respect to Example 1. Furthermore, this exemplary device 800 may be under the control of a command unit (not shown) that can be remotely located. This embodiment functions to replace the anal sphincter in the case of bowel resection. The illustrated bowel section 804 shown in phantom is prior to resection. As shown, the device 800 is positioned proximal the stoma 802. Such a device 800 may be used either at a normal anal location or at an existing ostomy site.

EXAMPLE 4

Pharmaceutical control vane

Figure 9:
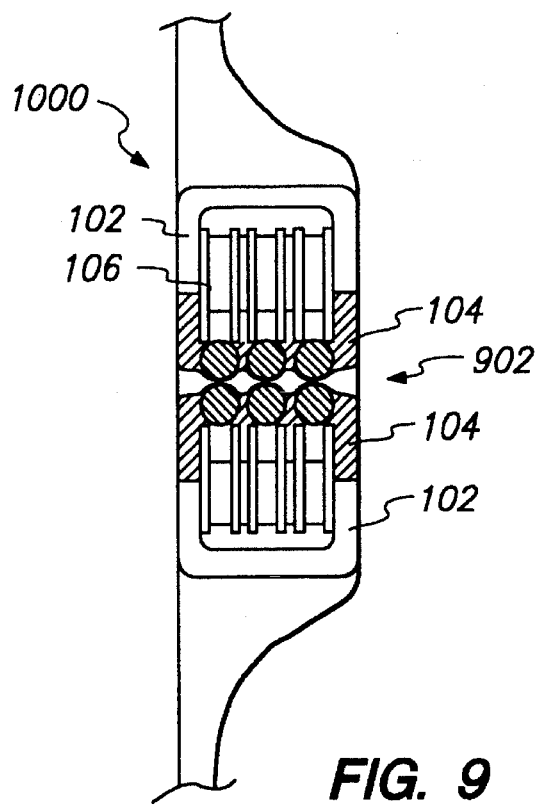
FIG. 9 shows a cross-section view of a control release drug dispensing device embodying the present invention.
Figure 10:
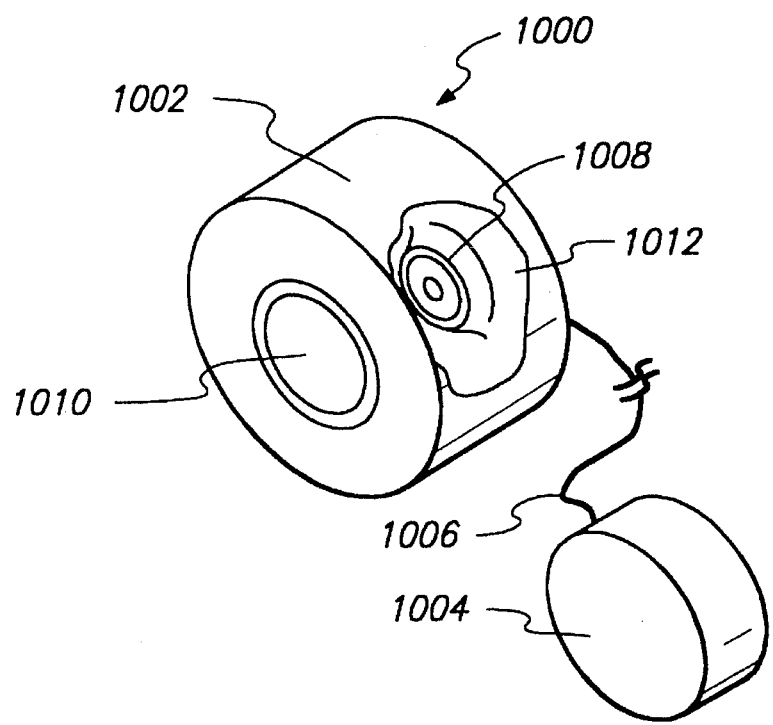
FIG. 10 shows a partial cut-away view of the drug delivery system of FIG. 9.

This exemplary device 1000, as shown in FIGS. 9 and 10, functions as a system for delivering drugs microencapsulated in inert, magnetic fluid containing spheroid carriers. The carriers are located at an in vivo target site and the drugs are released by means of an external magnetic field under the control of a physician. The spheroid carriers are small enough to pass: 1.5 through the capillaries of the body to deliver the contained drug to the affected sites. Prior to injection, the physician places a highly localized magnetic flux at the target site by placing the patient in a controlled electromagnetic device, such as a nuclear magnetic resonance (NMR) machine (available from General Electric, Schenectedy, N.Y.), or by a localized microelectromagnet under manual control. Once the magnetic field has been established, the drug encapsulating spheroids are injected into the bloodstream. As the spheroids flow through the bloodstream, they eventually pass through the site that it targeted by the magnetic flux and the magnetic field will nullify the micro-magnetic force that maintains their magnetorheological "valve" 902 in the closed position. With the valve 902 of the spheroid held open, the drug is released into the local tissue under the physician's control. Although some of the spheroids are removed from the bloodstream by normal cleansing functions prior to releasing their contained drug, the majority of them will function prior to being flushed from the body.

The illustrated exemplary device 1000 of FIGS. 9 and 10 controls the release of a drag from an in situ reservoir 1002. This device 1000 is under the control of a control unit 1004 containing a microcontroller, microelectronic interface circuitry, and an energy source such as a lithium battery pack of the type described above. This unit 1004 is connected by control wires 1006 to the inert magnetorheological fluid valve 1008. The operation of the device 1000 occurs when the preprogrammed algorithm of the control unit 1004 determines that the drug release is appropriate. The control unit 1004 may be programmed for dispensing drugs based on temporal settings, such as time in hours, physical indicators such as blood pressure, or biological reactions such as blood glucose. The storage reservoir 1002 for the drug may be in the shape of a flat cylinder or "pancake" and may be placed subcutaneously near the skin surface with an appropriate septum 1010 for sealing off the reservoir 1002 after periodic refilling from external hypodermic injections through the septum 1010.

When the control unit 1004 authorizes the release of the drug into the bloodstream, the control unit 1004 commands the relaxation of the first magnetorheological fluid valve 1008. When this valve 1008 relaxes, the atrium 1012 between the first 1008 and second valve 1014 fills with an aliquot of the drug from the reservoir 1002. The first valve 1008 then is returned to its normal, closed position and the second magnetorheological valve 1014 is commanded open as the atrium 1012 is constricted by the functioning of a third magnetorheological valve 1016 located coaxial to the atrium 1012. This action allows the contents of the reservoir 1002 to be positively ejected into the bloodstream and prevents the backflow of material into the atrium 1012. As the final amount of drug is ejected, the second valve 1014 is released to its normally closed position and the atrium 1012 is relaxed. This process releases one aliquot of drug into the user's blood system in a controlled manner. Further aliquots of drug may be released in rapid sequence to achieve the necessary dose level within the patient in a peristaltic type of action.

EXAMPLE 5

Carotid artery control mechanism

Figure 11:
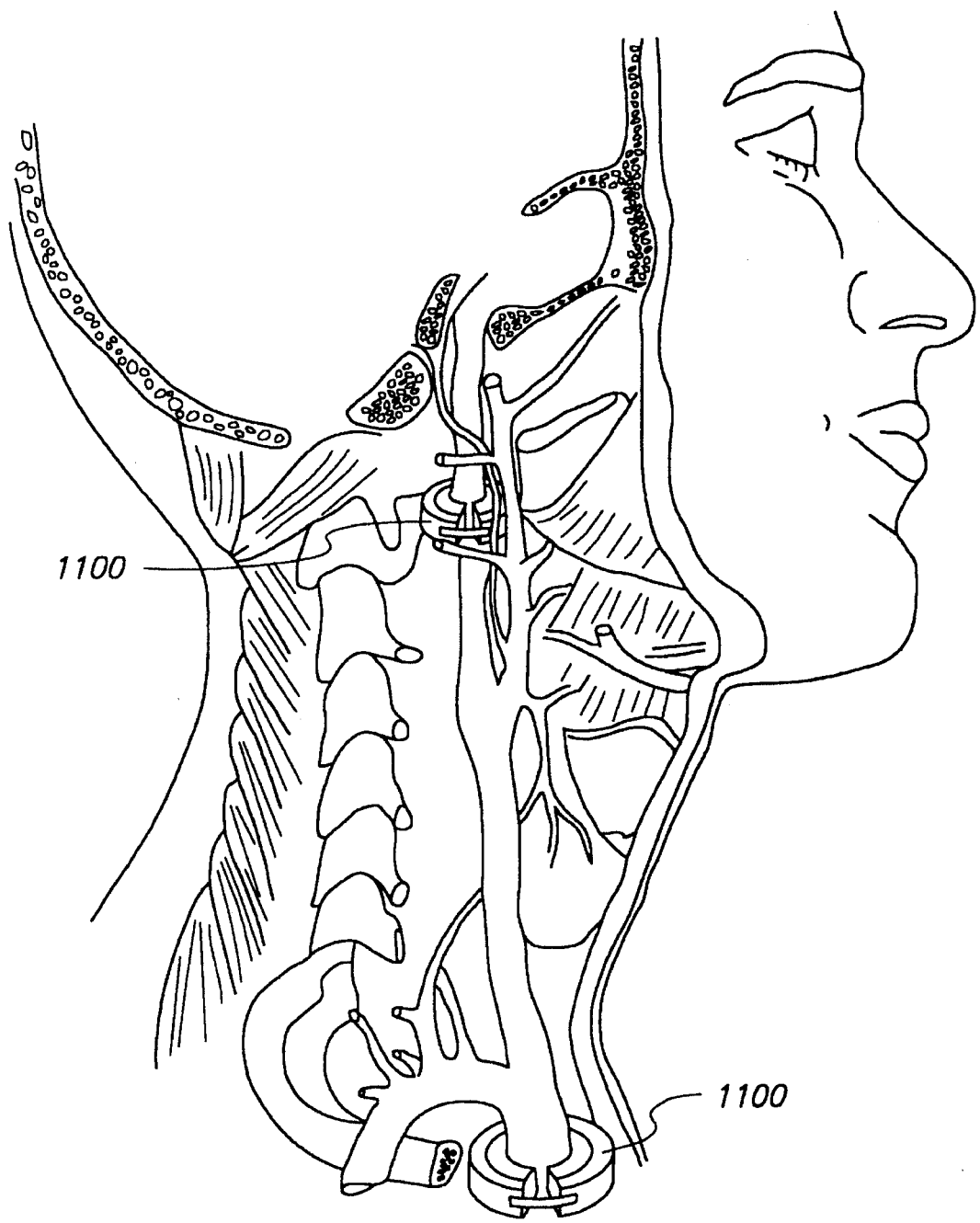
FIG. 11 is a partial cut-away view of a human neck showing a carotid artery control device embodying the present invention.

This exemplary device 1100, shown in FIG. 11, maintains and controls high blood pressure. This embodiment operates at blood pressure levels sufficient to prevent the occurrence of a cerebral vascular accident, such as a stroke, or an aneurysm. The device 1100 includes a pliable inner chamber 104 filled with a magnetorheological fluid 105, as described in detail above. An actuation mechanism 106 surrounds the chamber 104 and is controlled by a remotely located control unit 112.

In one embodiment, the carotid artery control mechanism 1100 is placed in an accessible body location that would mime patient discomfort and that would result in the least amount of collateral circulatory impairment. For example, individuals using such a device 1100 for aggressive positive-"G" performance would likely have such a device 1100 in a subclavian location, while an individual suffering from an aneurysm may have the device 1100 positioned in a submandibular position. In a preferred embodiment, the device 1100 is an interrupted toroidal shape with a gated opening. Since the carotid artery is approximately 15 mm in diameter, the opening within the toroid would be at least that size to prevent unnecessary circulatory constriction.

Construction of this exemplary controlling device 1100, battery containment, and the actuators, preferably housed in a rigid containment housing, would be of: titanium or titanium alloys such as Ti-6Al-4V; cobalt based ferrous alloys; nickel alloys, such as nickel-titanium alloys; ceramic materials, such as high density aluminum oxide; carbon compounds, such as pyrolytic carbon, vitreous carbon, or vapor deposited carbon on substrates; and plastic materials, such as medical grades of polyethylene, polypropylene, perfluorinated polymers, acrylic polymers, polyurethanes, and silicone rubbers.

There are many other exemplary uses for the inventive control device 100 described above and as claimed herein. Other embodiments include: peristaltic pump; surgical blood loss control device; anti-blackout device; magnetorheological obturator cuff; cardiac massage device; artificial heart valve; artificial pyloric valve; artificial esophagus; and pressure applicator.

What is claimed is:

1. A controllable valve apparatus for operation about a constrictable passageway, comprising:
    A. a flexible, formable, tubular housing adapted to be positioned around the passageway, including:
        (i) an extensible inner chamber extending at least partially along an outer surface of the housing, and
        (ii) at least one magnetic flux inductor device proximal to the inner chamber;
    B. a control device in communication with the magnetic flux inductor device for selectively activating the magnetic flux inductor device; and C. a quantity of a magnetorheological material responsive to activation of the magnetic flux inductor and contained within the inner chamber to cause the magnetorheological material to outwardly extend the inner chamber and constrict the passageway.

2. The valve apparatus of claim 1, wherein the tubular housing of predetermined length forms an open circle adapted to position the tubular housing around the passageway to be constricted.

3. The valve apparatus of claim 1, wherein the magnetorheological material further comprises a suspension of magnetic material.

4. The valve apparatus of claim 3, wherein the magnetorheological material further comprises an inert liquid suspension medium.

5. The valve apparatus of claim 3, wherein the magnetorheological material further comprises a quantity of ferrous microspheres.

6. The valve apparatus of claim 5, wherein the magnetorheological material further comprises an inert paraffinic suspension medium.

7. The valve apparatus of claim 1, wherein the magnetic flux inductor device comprises a magnetic material.

8. The valve apparatus of claim 1, further comprising a plurality of magnetic flux inductor devices proximal to the inner chamber.

9. The valve apparatus of claim 1, wherein the control device further comprises a programmable element for selectively controlling the magnetic flux inductor.

10. A prosthetic urinary incontinence apparatus for controllably constricting the urethra, comprising:
    A. a flexible, formable, tubular housing adapted to be positioned around the urethra, including:
        (i) an extensible inner chamber extending at least partially along an outer surface of the housing, and
        (ii) at least one magnetic flux inductor device proximal to the inner chamber;
    B. a control device in communication with the magnetic flux inductor device, for selectively activating the magnetic flux inductor device; and
    C. a quantity of a magnetorheological material responsive to activation of the magnetic flux inductor and contained within the inner chamber to cause the magnetorheological material to outwardly extend the inner chamber about the urethra for controllable constriction thereof.

11. The valve apparatus of claim 10, wherein the tubular housing forms an open circle adapted to position the tubular housing around the urethra.

12. The valve apparatus of claim 10, wherein the magnetorheological material further comprises a suspension of magnetic material.

13. The valve apparatus of claim 12, wherein the magnetorheological material further comprises an inert liquid suspension medium.

14. The valve apparatus of claim 12, wherein the magnetorheological material further comprises a quantity of ferrous microspheres.

15. The valve apparatus of claim 14, wherein the magnetorheological material further comprises an inert paraffinic suspension medium.

16. The valve apparatus of claim 10, wherein the magnetic flux inductor device comprises a magnetic material.

17. The valve apparatus of claim 10, further comprising a plurality of magnetic flux inductor devices proximal to the inner chamber.

18. The valve apparatus of claim 10, wherein the control device further comprises a programmable element for selectively controlling the magnetic flux inductor.

19. A controllable valve apparatus for operation within an expandable passageway, comprising:
    A. a flexible, formable, tubular housing adapted to be positioned within the passageway, including:
        (i) an extensible chamber extending at least partially along an outer surface of the housing, and
        (ii) at least one magnetic flux inductor device proximal to the chamber;
    B. a control device in communication with the magnetic flux inductor device for selectively activating the magnetic flux inductor device; and
    C. a quantity of a magnetorheological material responsive to activation of the magnetic flux inductor and contained within the chamber to cause the magnetorheological material to outwardly extend the chamber and expand the passageway.

20. The valve apparatus of claim 19, wherein the tubular housing forms an open circle adapted to position the tubular housing within a structure to be expanded.

21. The valve apparatus of claim 20, wherein the magnetorheological material further comprises a suspension of magnetic material.

22. The valve apparatus of claim 21, wherein the magnetorheological material further comprises an inert liquid suspension medium.

23. The valve apparatus of claim 21, wherein the magnetorheological material further comprises a quantity of ferrous microspheres.

24. The valve apparatus of claim 23, wherein the magnetorheological material further comprises an inert paraffinic suspension medium.

25. The valve apparatus of claim 19, wherein the magnetic flux inductor device comprises a magnetic material.

26. The valve apparatus of claim 19, further comprising a plurality of magnetic flux inductor devices proximal to the outer chamber.

27. The valve apparatus of claim 19, wherein the control device further comprises a programmable element for selectively Controlling the magnetic flux inductor.

28. A method of selectively controlling fluid flow through a constrictable structure using a flexible tubular housing, wherein the housing comprises:
    an inner chamber, containing a quantity of magnetorheological material, extending at least partially along an outer surface of the housing; and
    at least one magnetic flux inductor device proximal to the chamber; the method comprising the steps of:
        A. at least partially surrounding a selected portion of the structure with the flexible tubular housing; and then
        B. selectively expanding the housing by activating the inductor device to maintain the magnetorheological material in a first, expanded state to constrict the portion of the structure surrounded by the housing.

29. The method of claim 28, further comprising selectively contracting the housing by deactivating the inductor device to maintain the magnetorheological material in a second, relaxed state to allow the fluid flow through the constrictable structure.

30. A method of selectively controlling fluid flow through a constrictable structure using a flexible tubular housing, wherein the housing comprises:
    an inner chamber, containing a quantity of a magnetorheological material, extending at least partially along the length of the housing; and
    at least one magnetic flux inductor device, proximal to the chamber; the method comprising the steps of:

A. at least partially surrounding a selected portion of the structure with the housing;
B. activating the magnetic flux inductor device to expand the magnetorheological material in the housing to constrict the portion of the structure surrounded by the housing; and then
C. selectively deactivating the magnetic flux inductor device to release the constricted portion of the structure and to allow fluid flow through the structure.

\* \* \* \* \*